United States Patent

Fuss et al.

Patent Number: 5,547,605
Date of Patent: Aug. 20, 1996

[54] 2-ARYLOXYTETRAFLUOROPROPIONIC ESTERS, PROCESS FOR THEIR PREPARATION, AND THEIR USE IN LIQUID-CRYSTALLINE MIXTURES

[75] Inventors: Robert Fuss, Kelheim; Javier Manero, Frankfurt; Dietmar Jungbauer, Weiterstadt, all of Germany

[73] Assignee: Hoechst Aktiengesellschaft, Frankfurt, Germany

[21] Appl. No.: 354,666

[22] Filed: Dec. 13, 1994

[30] Foreign Application Priority Data

Dec. 15, 1993 [DE] Germany ............... 43 42 756.1

[51] Int. Cl.$^6$ ............... C09K 19/06; C09K 19/34; C09K 19; C09K 30; G02F 1/13
[52] U.S. Cl. ............... 252/299.6; 252/299.61; 252/299.63; 252/299.66; 252/299.67; 252/299.62; 359/103
[58] Field of Search ............ 252/299.61, 299.01, 252/299.6, 299.66, 299.63, 299.62, 299.67; 544/296, 298

[56] References Cited

U.S. PATENT DOCUMENTS 4,874,545 10/1989 Heppke et al. ............ 252/299.61

FOREIGN PATENT DOCUMENTS 1593046 7/1966 Germany .

Primary Examiner—Cynthia Harris Kelly
Attorney, Agent, or Firm—Curtis, Morris & Safford, P.C.

[57] ABSTRACT

The use of a compound of the formula I, in liquid crystal mixtures, $$R^1(-A^1)_a(-M^1)_b(-A^2)-O-CF(CF_3)-COO-(-A^3)(-M^2)_c(-A^4)_d-R^2 \quad I$$

in which the symbols and indices have the following meanings:

$R^1$ and $R^2$ are identical or different and are hydrogen, a straight-chain or branched alkyl radical having 1 to 20 carbon atoms (with or without asymmetrical carbon atoms), where one or more —$CH_2$— groups may also be replaced by —O—, —CO—, cyclopropane-1,2-diyl, —$Si(CH_3)_2$—, with the proviso that oxygen atoms must not be bonded directly to one another, and/or one or more H atoms of the alkyl radical may be substituted by —F; $M^1$ and $M^2$ are identical or different and are —CO—O—, —O—CO—, or a single bond;

$A^1$, $A^2$, $A^3$ and $A^4$ are identical or different and are 1,4-phenylene, in which one or more H atoms may be replaced by F, pyrazine-2,5-diyl, in which one or two H atoms may be replaced by F, pyridazine-3,6-diyl, in which one or two H atoms may be replaced by F, pyridine-2,5-diyl, in which one or more H atoms may be replaced by F, pyrimidine-2,5-diyl, in which one or two H atoms may be replaced by F, trans-1,4-cyclohexylene, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, 1,3-thiazole-2,5-diyl, in which one H atom may be replaced by F, thiophene-2,4-diyl, in which one H atom may be replaced by F, thiophene-2,5-diyl, in which one or two H atoms may be replaced by F, naphthalene-2,6-diyl, in which one or more H atoms may be replaced by F;

a, b, c and d are zero or one.

7 Claims, No Drawings

2-ARYLOXYTETRAFLUOROPROPIONIC ESTERS, PROCESS FOR THEIR PREPARATION, AND THEIR USE IN LIQUID-CRYSTALLINE MIXTURES

In addition to nematic and cholesteric liquid crystals, optically active tilted smectic (ferroelectric) liquid crystal phases have also been used recently in commercial display devices.

Clark and Lagerwall have been able to show that the use of ferroelectric liquid crystal systems in very thin cells results in optoelectrical switching or display elements which have response times faster by a factor of 1000 compared with conventional TN ("twisted nematic") cells (cf., for example, EP-A 0 032 362). On the basis of this and other favorable properties, for example the possibility of bistable switching and the virtually viewing angle-independent contrast, FLCs are fundamentally highly suitable for the above-mentioned areas of application, for example via matrix addressing.

For electro-optical or fully optical components, either compounds are required which form tilted or orthogonal smectic phases and are themselves optically active, or ferroelectric smectic phases can be induced by doping compounds which, although forming such smectic phases, are not themselves optically active, with optically active compounds. The desired phase should be stable over the broadest possible temperature range.

In order to achieve good contrast in electro-optical components, a uniform planar alignment of the liquid crystals is necessary. Good alignment in the $S_A$ and $S^*_C$ phase can be achieved, for example, if the phase sequence of the liquid-crystal mixture is, with decreasing temperature:

$$\text{isotropic} \rightarrow N^* \rightarrow S_A \rightarrow S^*_C$$

The prerequisite is that the pitch of the helix in the $N^*$ phase is very large (greater than 10 µm) or even better is fully compensated (see, for example, T. Matsumoto et al., pp. 468–470, Proc. of the 6th Int. Display Research Conf., Japan Display, Sep. 30–Oct. 2, 1986, Tokyo, Japan; M. Murakami et al., ibid. pp. 344–347). This is achieved by adding one or more optically active dopes which induce a right-hand helix to the chiral liquid-crystal mixture which has, for example, a left-hand helix in the $N^*$ phase, in such amounts that the helix is compensated.

A further prerequisite for the use of the SSFLCD effect (surface-stabilized ferroelectric liquid-crystal display) of Clark and Lagerwall for uniform planar alignment is that the pitch in the smectic $C^*$ phase is significantly greater than the thickness of the display element (Mol. Cryst. Liq. Cryst. 94 (1983), 213–134 and 114 (1984), 151–187). As in the case of the cholesteric pitch, this is achieved by using dopes having the opposite rotation of the helix.

Ferroelectric liquid-crystal displays can also be operated by utilizing the DHF (distorted helix formation) effect or the PSFLCD effect (pitch-stabilized ferroelectric liquid-crystal display, also known as SBF=short pitch bistable ferroelectric effect). The DHF effect has been described by B. I. Ostrovski in Advances in Liquid Crystal Research and Applications, Oxford/Budapest, 1980, 469 ff.; the PSFLCD effect is described in DE-A 39 20 625 and EP-A 0 405 346. In contrast to the SSFLCD effect, utilization of these effects requires a liquid-crystalline material having a short $S_C$ pitch.

The optical response time T[µs] of ferroelectric liquid-crystal systems, which should be as short as possible, depends on the rotational viscosity of the system Y[mPas], the spontaneous polarization $P_S$[nC/cm$^2$] and the electric field strength E[V/m], in accordance with the equation $$\tau \sim \frac{Y}{P_s \cdot E}$$

Since the field strength E is determined by the electrode separation in the electro-optical component and by the applied voltage, the ferroelectric display medium must have low viscosity and a high spontaneous polarization to achieve a short response time.

Finally, in addition to thermal, chemical and photochemical stability, a small optical anisotropy Δn, preferably ≈0.13, and a low positive or preferably negative dielectric anisotropy Δε are required (see S. T. Lagerwall et al., "Ferroelectric Liquid Crystals for Displays", SID Symposium, October Meeting 1985, San Diego, Calif., USA).

The totality of these requirements can only be achieved by means of mixtures comprising a plurality of components. The base (or matrix) used preferably comprises compounds which if possible themselves already have the desired phase sequence $I \rightarrow N \rightarrow S_A \rightarrow S_C$. Further components of the mixture are frequently added in order to reduce the melting point and to broaden the $S_C$ and usually also the N phase, to induce optical activity, for pitch compensation and to match the optical and dielectric anisotropy; however, the rotational viscosity, for example, should if possible not be increased.

Since the development of ferroelectric liquid-crystal mixtures in particular can in no way be regarded as complete, the manufacturers of displays are interested in a very wide variety of components for mixtures. Another reason for this is that only the interaction of the liquid-crystalline mixtures with the individual components of the display device or of the cells (for example the alignment layer) allows conclusions to be drawn on the quality of the liquid-crystalline mixtures too.

The object of the present invention was therefore to provide novel compounds which are suitable in liquid-crystalline mixtures for improving the property profile of these mixtures.

2-Phenoxytetrafluoropropionic acid and the phenyl ester thereof are disclosed in DE-A-1 593 046. However, the preparation process described therein gives only unsatisfactory yields and is technically complex. There is no mention of the use of such substances in liquid-crystal mixtures.

Surprisingly, it has now been found that aryl, heteroaryl and cyclohexyl esters of 2-aryloxytetrafluoropropionic acid are suitable as components of liquid-crystal mixtures.

The invention therefore relates to the use of 2-aryloxytetrafluoropropionic esters of the formula (I)

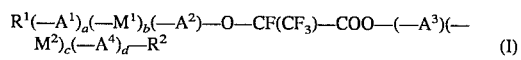

in which the symbols and indices have the following meanings:

$R^1$ and $R^2$ are identical or different and are hydrogen, —CN, —F, —Cl or a straight-chain or branched alkyl radical having 1 to 20 carbon atoms (with or without asymmetrical carbon atoms), where one or more —CH$_2$— groups may also be replaced by —O—, —S—, —CO—, —CS—, —CH=CH—, —C≡C—, cyclopropane-1,2-diyl, —Si(CH$_3$)$_2$—, 1,4-phenylene, trans-1,4-cyclohexylene or trans-1,3-cyclopentylene, with the proviso that oxygen atoms and sulfur atoms (referred to as chalcogens below) must not be bonded directly to one another, and/or one or more H atoms of the alkyl radical may be substituted by —F, —Cl, —Br, —OR³, —SCN, —OCN or —N₃, or are alternatively one of the following chiral groups:

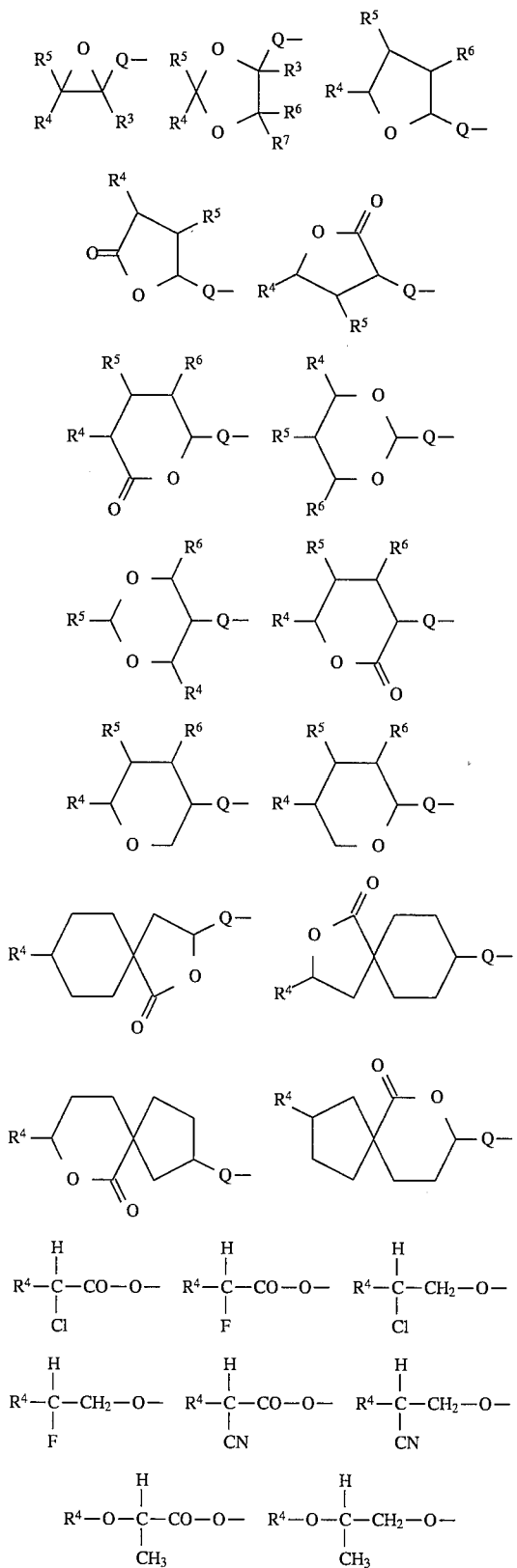

$R^3$, $R^4$, $R^5$, $R^6$ and $R^7$ are identical or different and are hydrogen or a straight-chain or branched alkyl radical having 1–16 carbon atoms (with or without asymmetrical carbon atoms), where one or more —CH₂— groups may also be replaced by —O— or —CH=CH—, with the proviso that oxygen atoms must not be bonded directly to one another, and/or one or more H atoms of the alkyl radical may be substituted by —F or —Cl; $R^4$ and $R^5$ may also together be —(CH₂)₄— or —(CH₂)₅— if they are bonded to an oxirane, dioxolane, tetrahydrofuran, tetrahydropyran, butyrolactone or valerolactone system;

Q is a single bond, —CO—O— or —CH₂—O—;

$M^1$ and $M^2$ are identical or different and are —O—, —S—, —CO—, —CO—O—, —O—CO—, —O—CO—O—, —CO—S—, —S—CO—, —CS—O—, —O—CS—, —S—CS—S—, —O—C S—O—, —S—CO—S—, —CS—, —CH₂—O—, —O—CH₂—, —CH₂—S—, —S—CH₂—, —CH=CH—, —C≡C— or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH₃, 1,3,4-thiadiazole-2,5-diyl, 1,3-dioxane- 2,5-diyl, 1,3-dithiane-2,5-diyl, 1,3-thiazole-2,4-diyl, in which one H atom may be replaced by F, Cl and/or CN, 1,3-thiazole-2,5-diyl, in which one H atom may be replaced by F, Cl and/or CN, thiophene- 2,4-diyl, in which one H atom may be replaced by F, Cl and/or CN, thiophene-2,5-diyl, in which one or two H atoms may be replaced by F, Cl and/or CN, piperazine-1,4-diyl, piperazine-2,5-diyl, naphthalene-2,6-diyl, in which one or more H atoms may be replaced by F, Cl and/or CN, bicyclo[2.2.2]octane-1,4-diyl, in which one or more H atoms may be replaced by F, Cl and/or CN, or 1,3-dioxaborinane-2,5-diyl;

a, b, c and d are zero or one;

as components of liquid-crystal mixtures.

If $R^1$ and/or $R^2$ are one of the optically active or racetalc groups mentioned, the indices a and d are preferably zero.

Preference is furthermore given to the use of compounds of the formula (I) in which the symbols and indices have the following meanings:

$R^1$ and $R^2$ are identical or different and are hydrogen, —CN, —F, —Cl or a straight-chain or branched alkyl radical having 1 to 18 carbon atoms (with or without asymmetrical carbon atoms), where one or more —CH₂— groups may also be replaced by —O—, —CO—, —CH=CH—, —C≡C—, cyclopropane-1,2-diyl, —Si(CH₃)₂— or trans-1,4-cyclohexylene, with the proviso that oxygen atoms must not be bonded directly to one another, and/or one or more H atoms of the alkyl radical may be substituted by —F, —Cl, —OR³, —OCN or —N₃, or are one of the following chiral groups:

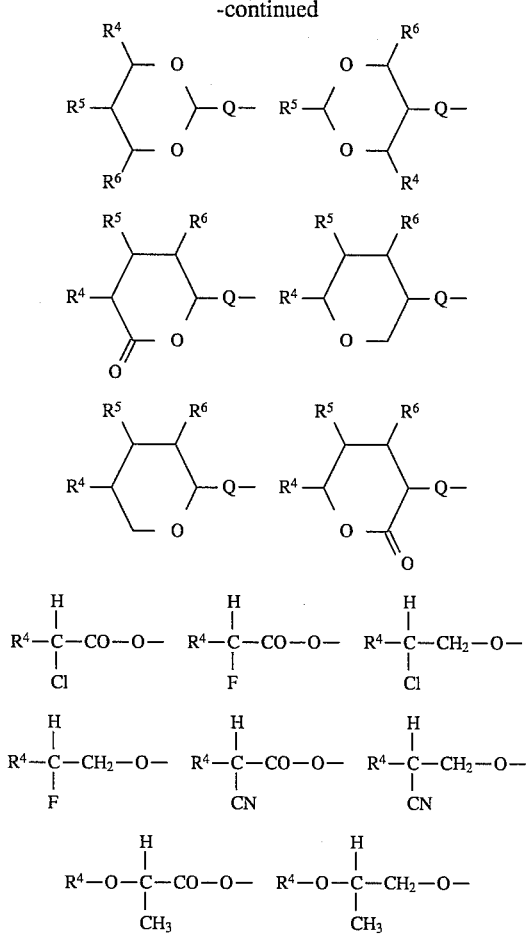

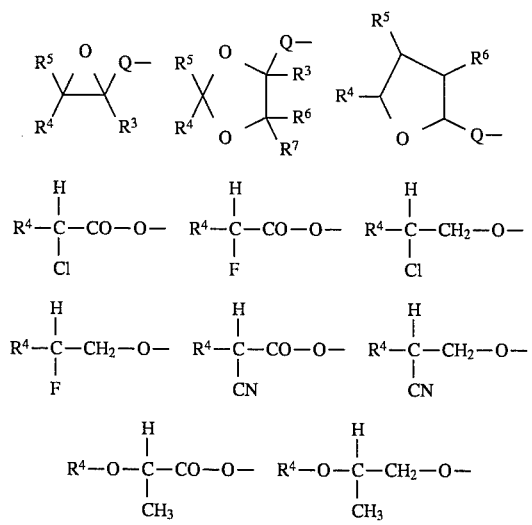

be replaced by F, Cl and/or CN, or 1,3-dioxaborinane-2,5-diyl;

a, b, c and d are zero or one.

Very particular preference is given to the use of compounds of the formula (I) in which the symbols and indices have the following meanings:

$R^1$ and $R^2$ are identical or different and are hydrogen, —CN, —F, —Cl, or a straight-chain or branched alkyl radical having 1 to 16 carbon atoms (with or without asymmetrical carbon atoms), where one, two or three —CH$_2$— groups may also be replaced by —O—, —CO—, —CH=CH—, cyclopropane-1,2-diyl, —Si(CH$_3$)$_2$— or trans-1,4-cyclohexylene, with the proviso that oxygen atoms must not be bonded directly to one another, and/or one or more H atoms of the alkyl radical may be substituted by —F, —Cl or —OR$^3$, or are alternatively one of the following chiral groups:

$R^3$, $R^4$, $R^5$, $R^6$ and $R^7$ are identical or different and are hydrogen or a straight-chain or branched alkyl radical having 1–16 carbon atoms (with or without asymmetrical carbon atoms), where one or more —CH$_2$— groups may also be replaced by —O— or —CH=CH—, with the proviso that oxygen atoms must not be bonded directly to one another, and/or one or more H atoms of the alkyl radical may be substituted by —F or —Cl; $R^4$ and $R^5$ may also together be —(CH$_2$)$_4$— or —(CH$_2$)$_5$— if they are bonded to an oxirane, dioxolane, tetrahydrofuran, tetrahydropyran, butyrolactone or valerolactone system;

Q is a single bond, —CO—O— or —CH$_2$—O—;

$M^1$ and $M^2$ are identical or different and are —O—, —CO—, —CO—O—, —O—CO—, —O—CO—O—, —O—CS—O—, —CH$_2$—O—, —O—CH$_2$—, —CH=CH—, —C≡C— or a single bond;

$A^1$, $A^2$, $A^3$ and $A^4$ are identical or different and are 1,4-phenylene, in which one or more H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or more H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH$_3$, 1,3,4-thiadiazole-2,5-diyl, 1,3-dioxane-2,5-diyl, thiophene-2,4-diyl, in which one H atom may be replaced by F, Cl and/or CN, thiophene-2,5-diyl, in which one or two H atoms may be replaced by F, Cl and/or CN, naphthalene-2,6-diyl, in which one or more H atoms may $R^3$, $R^4$, $R^5$, $R^6$ and $R^7$ are identical or different and are hydrogen or a straight-chain or branched alkyl radical having 1–14 carbon atoms (with or without asymmetrical carbon atoms), where one or more —CH$_2$— groups may also be replaced by —O— or —CH=CH—, with the proviso that oxygen atoms must not be bonded directly to one another, and/or one or more H atoms of the alkyl radical may be substituted by —F or—Cl; $R^4$ and $R^5$ may also together be —(CH$_2$)$_4$— or —(CH$_2$)$_5$— if they are bonded to an oxirane or dioxolane system;

Q is a single bond, —CO—O— or—CH$_2$—O—;

$M^1$ and $M^2$ are identical or different and are —O—, —CO—, —CO—O—, —O—CO—, —O—CO—O—, —CH$_2$—O—, —O—CH$_2$—, —CH=CH— or a single bond;

$A^1$, $A^2$, $A^3$ and $A^4$ are identical or different and are 1,4-phenylene, in which one, two or three H atoms may be replaced by F, Cl and/or CN, pyrazine-2,5-diyl, in which one or two H atoms may be replaced by F, Cl and/or CN, pyridazine-3,6-diyl, in which one or two H atoms may be replaced by F, Cl and/or CN, pyridine-2,5-diyl, in which one or two H atoms may be replaced by F, Cl and/or CN, pyrimidine-2,5-diyl, in which one or two H atoms may be replaced by F, Cl and/or CN, trans-1,4-cyclohexylene, in which one or two H atoms may be replaced by CN and/or CH$_3$, 1,3,4-thiadiazole-2,5-diyl, naphthalene-2,6-diyl, in which one or two H atoms may be replaced by F, Cl and/or CN, or 1,3-dioxaborinane-2,5-diyl;

a, b, c and d are zero or one.

Very particular preference is given to compounds of the formula (I) in which the alcohol and ester components are identical. The compounds of the formula (I) are employed as optically active components or as the racemate.

The invention furthermore relates to compounds of the formula (I), in which the abovementioned definitions apply, but phenyl phenoxytetrafluoropropionate is excluded.

The novel compounds can be prepared by the process described in DE-A-1 593 046.

However, preference is given to a novel preparation process, which is likewise a subject-matter of the present invention.

In this process, hexafluoropropene oxide is passed at atmospheric pressure into an arylate solution, and the aryl 2-aryloxytetrafluoropropionate formed is isolated, saponified if desired and, if desired, re-esterified in a further step.

Preferred arylates are metal or ammonium salts, preferably alkali metal or alkaline earth metal salts, particularly preferably sodium salts, of compounds of the formula (II)

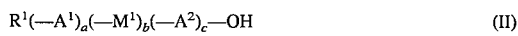

$R^1(—A^1)_a(—M^1)_b(—A^2)_c—OH$        (II)

in which the symbols and indices have the same definitions and preferences as in the formula (I).

Hexafluoropropene oxide is commercially available.

In order to carry out the reaction, the arylate is introduced into a suitable solvent, and hexafluoropropene oxide is passed into the solution at room temperature. In general, an exothermic reaction immediately takes place, which can be controlled, for example, by throttling the hexafluoropropene oxide stream. When the reaction is complete, unreacted hexafluoropropene oxide begins to condense in the reflux condenser, thus indicating the end of the reaction.

The reaction is generally carried out at temperatures of from 10° to −30° C., preferably from 0° to −10° C., particularly preferably −10° C.

The solvents used are generally dipolar aprotic solvents, preferably ethers, particularly preferably glycol ethers, in particular diglyme and tetraglyme.

The work-up can be carried out by standard methods, for example by pouring into an ice/water mixture, followed by extraction with a suitable solvent, for example diethyl ether, methylene chloride or t-butyl methyl ether, followed by drying, for example by means of magnesium sulfate. Removal of the solvent gives the crude product, which can be purified, for example by column chromatography, for example on $SiO_2$, using a suitable solvent (for example heptane, methylene chloride, methanol, ethyl acetate or mixtures thereof).

In order to prepare compounds of the formula (I) using different ether and ester components, the resultant ester is cleaved and the acid liberated or a salt thereof is esterified, for example using a compound of the formula (III),

$R^2—(A^4—)_g(M^3—)_f(—A^3)—X$        (III)

where the symbols and indices have the meanings and preferences given in the formula (I), X is OH or a reactive group which is capable of esterification.

The ester cleavage is carried out, for example, by hydrolysis in an acidic, neutral or basic medium, preferably in a basic medium. The subsequent esterification by means of the compound (III) is carried out by general esterification reactions known to the person skilled in the art. Esterification methods are described, for example, in A. Hassner and V. Alexanian, Tet. Lett. 46 (1978) 4478, (a) R. B. Turner, J.Am. Chem. Soc., 75 (1953) 3489; (b) E. Vowinkel, Chem. Ber., 100, (1967) 16; (c) H. Staab, Angew. Chem. Internat. Ed. 1 (1962) 351; (d) J. M. Tedder, Chem. Revs., 55 (1955) 787; (e) H. Brechbuehler, H. Buchl, E. Hatz, J. Schreiber and A. Eschenmoser, Helv. Chim. Acta, 48 (1965) 1746; (f) S. Masamune, S. Kamata and W. Schilling, J. Am. Chem. Soc. 97 (1975) 3515; (g) E. J. Corey and D. J. Brunella, Tetrahedron Letters (1976) 3409; and (h) T. Mukalyama, M. Usui and K. Saigo, Chem. Lett. 1976, 49, or in the German Patent Application P 43 26 336.4 with the title "Verfahren zur Veresterung von Carbonsäuresalzen" [Process for the esterification of carboxylic acid salts].

The yields in the novel process are significantly greater than those described hitherto, and the process can also be used for substituted phenols and can be carried out in a technically simple manner by the pressureless reaction procedure.

The synthesis of the $R^1(—A^1)_a(—M^1)_b(—A^2)$ and $(A^1)(M^2)_c(—A^4)_d—R^2$ radicals or suitable reactive derivatives thereof is carried out by methods known to the person skilled in the art.

The preparation is carried out under reaction conditions which are known and suitable for said reactions. Use may also be made here of variants which are known per se, but are not described here in greater detail.

For example, reference may be made to DE-A 23 44 732, 24 50 088, 24 29 093, 25 02 94, 26 36 684, 27 01 591 and 27 52 975 for compounds containing 1,4-cyclohexylene and 1,4-phenylene groups; DE-A 26 41 724 for compounds containing pyrimidine-2,5-diyl groups; DE-A 40 26 223 and EP-A 03 91 203 for compounds containing pyridine-2,5-diyl groups; DE-A 32 31 462 for compounds containing pyridazine-3,6-diyl groups; EP-A 309 514 for compounds containing 1,3,4-thiadiazole-2,5-diyl groups; WO-A 92/16500 for naphthalene-2,6-diyl groups; DE-A 37 10 890 for bicyclo[2.2.2]octane-1,4-diyl groups; K. Seto et al., Journal of the Chemical Society, Chemical Communications 1988, 56, for dioxoborinane-2,5-diyl groups.

The preparation of disubstituted pyridines, disubstituted pyrazines, disubstituted pyrimidines and disubstituted pyridazines is also given, for example, in the corresponding volumes in the series "The Chemistry of Heterocyclic Compounds" by A. Weissberger and E. C. Taylor (Editors).

Dioxane derivatives are expediently prepared by reaction of a corresponding aldehyde (or a reactive derivative thereof) with a corresponding 1,3-diol (or a reactive derivative thereof), preferably in the presence of an inert solvent, such as benzene or toluene, and/or in the presence of a catalyst, for example a strong acid, such as sulfuric acid, benzenesulfonic acid or p-toluenesulfonic acid, at temperatures between about 20° C. and about 150° C., preferably between 80° C. and 120° C. Primarily suitable reactive derivatives of the starting materials are acetals.

Some of said aldehydes and 1,3-diols and reactive derivatives thereof are known and some can be prepared without difficulty by standard methods of organic chemistry from compounds known from the literature. For example, the aldehydes are obtainable by oxidation of corresponding alcohols or by reduction of nitriles or corresponding carboxylic acids or derivatives thereof, and the diols are obtainable by reduction of corresponding diesters.

Compounds in which an aromatic ring is substituted by at least one F atom can also be obtained from the corresponding diazonium salts by replacement of the diazonium group by a fluorine atom, for example by the methods of Balz and Schiemann.

As far as the linking of ring systems to one another is concerned, reference may be made, for example, to:

N. Miyaura, T. Yanagai and A. Suzuki in Synthetic Communications 11 (1981), 513–519 DE-C-39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165, 204 (1991) 43 and 91; EP-A 0 449 015; WO-A 89/12039; WO-A 89/03821; EP-A 0 354 434 for the direct linking of aromatics and heteroaromatics; DE-A 32 01 721 for compounds containing —$CH_2CH_2$— bridges, and Koji Seto et al. in Liquid Crystals 8 (1990) 861–870 for compounds containing —C≡C— bridges.

Esters of the formula (I) can also be obtained by esterification of corresponding carboxylic acids (or reactive derivatives thereof) using alcohols or phenols (or reactive derivatives thereof) or by the DCCl method (DCCl=dicyclohexylcarbodiimide).

The corresponding carboxylic acids and alcohols or phenols are known and can be prepared analogously to known processes.

Particularly suitable reactive derivatives of the said carboxylic acids are the acid halides, especially the chlorides and bromides, furthermore the anhydrides, for example also mixed anhydrides, azides or esters, in particular alkyl esters having 1–4 carbon atoms in the alkyl group.

Particularly suitable reactive derivatives of said alcohols and phenols are the corresponding metal alkoxides or phenoxides, preferably of an alkali metal, such as sodium or potassium.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

Ethers of the formula (I) are obtainable by etherification of corresponding hydroxyl compounds, preferably corresponding phenols, where the hydroxyl compound is expediently first converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This can then be reacted with the corresponding alkyl halide, sulfonate or dialkyl sulfate, expediently in an inert solvent, such as acetone, 1,2-dimethoxy-ethane, DMF or dimethyl sulfoxide, or alternatively with an excess of aqueous or aqueous/alcoholic NaOH or KOH at temperatures between about 20° and 100° C.

Regarding the synthesis of specific radicals $R^1$, reference may additionally be made, for example, to EP-A 0 355 008 for compounds containing silicon-containing side chains and to EP-A 0 292 954 and EP-A 0 398 155 for compounds containing cyclopropyl groups in the side chain.

The provision of compounds of the formula (I) very generally considerably broadens the range of liquid-crystalline substances which are suitable, from various application points of view, for the preparation of liquid-crystalline mixtures.

In this connection, the compounds of the formula (I) have a broad range of applications. Depending on the choice of substituents, they can be used as base materials from which liquid-crystalline phases are predominantly composed; however, compounds of the formula (I) can also be added to liquid-crystalline base materials from other classes of compound, in order, for example, to modify the dielectric and/or optical anisotropy of a dielectric of this type and/or to optimize its threshold voltage and/or its viscosity. Optically active compounds of the formula (Ia) are preferably used as dopes in ferroelectric and/or antiferroelectric liquid-crystal mixtures.

The invention also relates to the use of compounds of the formula (I) in liquid-crystal mixtures, preferably ferroelectric, antiferroelectric and nematic, in particular in ferroelectric and antiferroelectric mixtures.

The invention furthermore relates to liquid-crystal mixtures, preferably ferroelectric, antiferroelectric and nematic mixtures, in particular ferroelectric and antiferroelectric mixtures, containing one or more compounds of the formula (I), preferably of the formula (Ia).

The liquid-crystal mixtures according to the invention generally contain from 2 to 35, preferably from 2 to 25, particularly preferably from 2 to 20 components.

They generally contain from 0.01 to 80% by weight, preferably from 0.1 to 60% by weight, particularly preferably from 0.1 to 30% by weight, of one or more, preferably 1 to 10, particularly preferably 1 to 5, very particularly preferably 1 to 3, of the compounds of the formula (I) according to the invention.

Further components of liquid-crystal mixtures containing compounds of the formula (I) according to the invention are preferably selected from known compounds having smectic and/or nematic and/or cholesteric and/or antiferroelectric phases. These include, for example:

derivatives of phenylpyrimidine, as described, for example, in WO 86/06401 and U.S. Pat. No. 4,874,542, meta-substituted aromatic compounds having a six-membered ring, as described, for example, in German Patent Application P 42 22 565, silicon compounds, for example, in EP-A 0 355 008, mesogenic compounds containing only one side chain as described in EP-A 0 541 081, hydroquinone derivatives, as described, for example, in German Patent Application P 4 243 705, pyridylpyrimidines, as described, for example, in WO 92/12974, phenylbenzoates, as described, for example, in P. Keller, Ferroelectrics 58 (1984), 3, and J. W. Goodby et al., Liquid Crystals and Ordered Fluids, Vol. 4, New York, 1984, and thiadiazoles as described, for example, in EP-B 309 514.

Examples of suitable chiral, non-racemic dopes are:

optically active phenylbenzoates, as described, for example, in P. Keller, Ferroelectrics 58 (1984), 3, and J. W. Goodby et al., Liquid Crystals and Ordered Fluids, Vol. 4, New York, 1984, optically active oxirane ethers, as described, for example, in EP-A 0 263 437 and WO-A 93/13093, optically active oxirane esters, as described, for example, in EP-A 0 292 954, optically active dioxolane ethers, as described, for example, in EP-A 0 351 746, optically active dioxolane esters, as described, for example, in EP-A 0 361 272, and optically active tetrahydrofuran-2-carboxylic esters, as described, for example, in EP-A 0 355 561.

The mixtures can in turn be used in electro-optical or fully optical elements, for example display elements, switching elements, light modulators, elements for image processing and/or signal processing or generally in the area of nonlinear optics.

Liquid-crystalline mixtures containing compounds of the formula (I) are particularly suitable for use in electro-optical switching and display devices (displays). These displays are usually constructed in such a way that a liquid-crystal layer is enclosed on both sides by layers which are usually, in this sequence starting from the LC layer, at least one alignment layer, electrodes and a limiting sheet (for example of glass). In addition, they contain spacers, adhesive frames, polarizers and, for color displays, thin color-filter layers. Other possible components are antireflection, passivation, compensation and barrier layers and electric non-linear elements, such as thin-film transistors (TFTs) and metal-insulator-metal (MIM) elements. The structure of liquid-crystal displays has already been described in detail in relevant monographs (see, for example, E. Kaneko, "Liquid Crystal TV Displays: Principles and Applications of Liquid Crystal Displays", KTK Scientific Publishers 1987).

The mixtures are furthermore suitable for field treatment, i.e. for operation in the quasi-bookshelf geometry (QBG) (see, for example, H. Rieger et al., SID 91 Digest (Anaheim), 1991, p. 396).

The mixtures according to the invention are likewise suitable for use in ferroelectric liquid-crystal displays which are based on utilization of the DHF effect or the PSFLCD effect (pitch stabilized ferroelectric liquid-crystal display, also known as SBF, short pitch bistable ferroelectric effect).

In addition, the compounds of the formula (I) can also be used as antiferroelectric liquid crystals or as components of corresponding mixtures.

Antiferroelectric liquid crystals are described, for example, in A. D. L. Chandani et al., Jap. J. of Appl. Phys. 27 (1988) L 729–L 732; A. D. Chandani et al., Jap. J. of Appl. Phys. 28 (1989) L 1265; H. Orihara et al., Jap. J. of Appl. Phys 29 (1990) L 333.

Electro-optical devices based on antiferroelectric liquid crystals are described, for example, in U.S. Pat. No. 5,046,823.

The novel compounds are furthermore suitable for achieving the so-called electroclinic effect in the chiral smectic A phase ($S^*_A$ phase) which can be utilized for light modulation (S. Garoff and R. B. Meyer, Phys. Rev. Lett. 38, 848 (1977)).

If an electric field is applied parallel to the layers of a chiral $S_A$ phase ($S^*_A$ phase), the molecules in the phase, which is orthogonal per se, tilt. The tilt angle θ between the director n̂ and the layer perpendicular ẑ is proportional to the applied field E. The electroclinic coefficient (dθ/dE) gives the strength of the linear coupling between the tilt coordinates and the field.

The electroclinic effect proceeds from a state which is monostable in the field-free space and gives, when a field is applied, a linear electro-optical characteristic line for small angles and a slightly curved electro-optical characteristic line for large angles. By contrast, the characteristic line for ferroelectric switching is highly nonlinear.

The electroclinic effect can be regarded as a change in the tilt angle which is continuously controlled by the field.

For practical utilization of the electroclinic effect in electro-optical switching and display elements, liquid-crystalline media which form an $S^*_A$, $S^*_B$ or $S^*_E$ phase are all the more suitable the larger the electroclinic coefficient dθ/dE and the higher the electroclinic limiting frequency $f_G$.

A device based on utilization of the electroclinic effect is given, for example, in Andersson et al., Appl. Phys. Lett. 1987, 51,640.

The invention is described in greater detail by means of the examples, but this is not intended to represent a limitation.

EXAMPLES

The phase-transition temperatures are determined from the changes in structure on heating with the aid of a polarizing microscope. By contrast, the melting point is determined using a DSC instrument. The phase-transition temperature data between the phases

| | |
|---|---|
| isotropic | (I) |
| nematic | (N or N*) |
| smectic C | ($S_C$ or $S_C$*) |
| smectic A | ($S_A$) |
| crystalline | (X) |
| glass transition | (Tg) | are given in ° C., and the values are between the phase designations in the phase sequence. Values in brackets are obtained during cooling.

EXAMPLE 1

4-(5-octyloxypyrimidin-2-yl)phenyl 2,3,3,3-tetrafluoro-2-[4-(5-octyloxypyrimidin-2-yl)phenoxy]propionate 4-[5-octyloxypyrimidin-2-yl]phenol (5.0 g; 17 mmol) is reacted with sodium hydride (0.6 g; 25 mmol) at room temperature in THF (60 ml) to give the corresponding phenoxide. At −10° C., hexafluoropropene oxide (3.5 g; 21 mmol) is passed in (dry-ice condenser), an exothermic reaction occurring. When the introduction is complete, the mixture is stirred for a further 1 hour and subsequently hydrolyzed carefully using ice-water. Conventional work-up and column chromatography (Ø 6 cm; length 0.5 m; SiO₂/CH₂Cl₂) give 2.9 g (50% of theory) of (1); m.p.: 84° C.

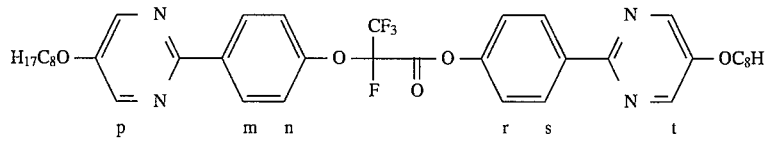

$^1$H-NMR: (360 MHz, 2% strength by weight solution in DMSO-d₆) δ=0.86 (m, 6 H, 2×CH₃), 1.29 (m, 20 H, 2×(CH₂)₅CH₃), 1.75 (m, 4 H, 2 ×(OCH₂CH₂)), 4.17 (m, 4 H, 2×(OCH₂)), 7.03 (d, $J_{HH}$=8.7 Hz, 2 H, n), 7.44 (d, $J_{HH}$=8.3 Hz, 2 H, r), 8.28 (d, $J_{HH}$=8.9 Hz, 2 H, m), 8.41 (d, $J_{HH}$=8.9 Hz, 2 H, s), 8.58 (s, 2 H, p), 8.63 (s, 2 H, t). $^{19}$F-NMR (338.9 MHz, 2% strength by weight solution in DMSO-d₆) δ=−80.2 (d, $J_{FF}$=3.8 Hz, 3 F, CF₃), −122.25 (m, 1 F, CF).

EXAMPLE 2

4-Decyloxyphenyl 2-(4-decyloxyphenoxy)-2,3,3,3-tetrafluoropropionate

4-Decyloxyphenol (3.0 g; 12 mmol) is reacted with sodium hydride (0.8 g; 33 mmol) at room temperature in dimethylformamide (30 ml) to give the corresponding phenoxide. At −10° C., hexafluoropropene oxide (2.0 g; 12 mmol) is passed in (dry-ice cooling), an exothermic reaction taking place. The mixture is subsequently stirred for an hour, subjected to conventional work-up and purified by column chromatography. Yield of (2): 2.97 g (79%). m.p. 48° C.

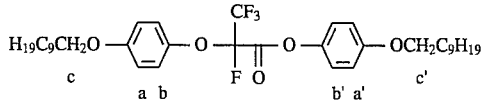

II $^1$H-NMR: (100 MHz, 5% strength by weight solution in CDCl$_3$) δ=0.87 (m, 6 H, 2×CH$_3$), 1.3 (m, 28 H, 2×(CH$_2$)$_7$CH$_3$), 1.75 (m, 4 H, 2×(OCH$_2$CH$_2$)), 3.88 (t, J$_{HH}$=5 Hz, OCH$_2$, c), 3.94 (t, J$_{HH}$=5 Hz, OCH$_2$, c'), 6.75 (m, 6 H, a,a', b), 7.2 (d, J$_{HH}$=12.5 Hz, b').

$^{19}$F-NMR (338.9 MHz, 2% strength by weight solution in DMSO-d$_6$) δ=−82.2 (d, J$_{FF}$=4 Hz, 3 F, CF$_3$), −123 (m, 1 F, CF).

EXAMPLE 3

Octyl 2,3,3,3-tetrafluoro-2-[4-(5-octyloxypyrimidin-2-yl)phenoxy]propionate

Compound (1) (8.0 g; 11 mmol) is refluxed for 1 hour in KOH solution (3.09 g (55 mmol) in 10 ml of H$_2$O) together with ethanol (50 ml). The mixture is subsequently acidified at room temperature using dilute aqueous HCl, and the residue is filtered off with suction. The aqueous phase is extracted with methylene chloride (3×50 ml), dried and evaporated. The residue obtained is combined with the first residue and chromatographed on an SiO$_2$ column (Ø 6 cm; length 0.5 m; CH$_2$Cl$_2$/ethyl acetate of 4:1). Yield: 3.29 g (65% of theory). The free acid obtained (1.0 g (23 mmol) is converted into the corresponding acid chloride in tetrahydrofuran (10 ml) using thionyl chloride (0.41 g (35 mmol)) using pyridine as auxiliary base (0.19 g (24 mmol)) and immediately esterified using n-octanol (0.32 g (24 mmol)). Crude yield 1.16 g (92% of theory). The product is purified by column chromatography (SiO$_2$; Ø4 cm; length 0.4 m; ethyl acetate) and subsequently recrystallized (acetonitrile). Phases: X 12 (−30) I; glass transition temperature −68° C.

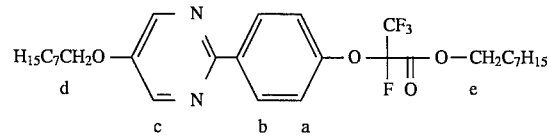

III $^1$H-NMR: (100 MHz, 5% strength by weight solution in CDCl$_3$) δ=0.83 (m, 3 H, CH$_3$), 1.3 (m, 10 H, (CH$_2$)$_5$CH$_3$), 1.6 (m, 2 H, OCH$_2$CH$_2$), 4.05 (m, 2 H, OCH$_2$, d), 4.12 (m, 2 H, OCH$_2$, e), 7.2 (d, J$_{HH}$=8 Hz, 2H, a), 8.3 (d, J$_{HH}$=8 Hz, b), 8.4 (s, 2 H) c).

$^{19}$F-NMR (94.2 MHz, 5% strength by weight solution in DMSO-d$_6$) δ=−80 (d, J$_{FF}$=4 Hz, 3 F, CF$_3$), −122 (m, 1 F, CF).

EXAMPLE 4

3,3,4,4,5,5,6,6,7,7,8,8,8-tridecafluorooctyl 2,3,3,3-tetrafluoro-2-[4-(5-octyloxypyrimidin-2-yl)phenoxy]propionate The free acid or acid chloride obtained analogously to Example 3 is esterified using perfluoro-1H,1H,2H,2H-octanol (0.87 g (24 mmol)). Crude yield 1.0 g (56% of theory).

The product is purified by column chromatography using acetonitrile as eluent, and subsequently recrystallized from the acetonitrile.

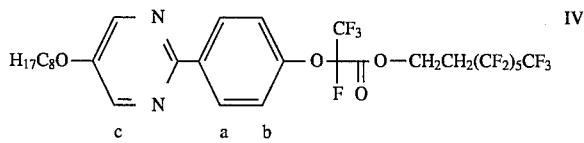

IV $^1$H-NMR: (100 MHz, 5% strength by weight solution in CDCl$_3$) δ=0.92 (m, 3 H, CH$_3$), 1.3 (m, 10 H, (CH$_2$)$_5$CH$_3$), 1.83 (m, 2 H, OCH$_2$CH$_2$RH), 2.28 (m, 2 H, CH$_2$R$_f$), 4.1 (t, J$_{HH}$=6 Hz, 2 H, —OCH$_2$—), 4.4 (t, J$_{HH}$=6 Hz, 2 H, —OCH$_2$CH$_2$R$_f$), 7.2 (d, J$_{HH}$=8.7 Hz, 2 H, a), 8.3 (d, J$_{HH}$=8.7 Hz, b), 8.43 (s, 2 H) c).

$^{19}$F-NMR (94.2 MHz, 5% strength by weight solution in CDCl$_3$) δ=−81 (m, 3 F, —CF$_2$CF$_3$), −81.5 (d, J$_{FF}$=4 Hz, 3 F, CF$_3$), −113 (m, 2 F, —CF$_2$CF$_3$), −122 (m, 2 F, —CF$_2$CF$_2$CF$_3$), −123 (m, 2 F, CH$_2$CF$_2$CF$_2$—), −124 (m, 1 F, CF), −126.4 (m, 2 F, —CH$_2$CF$_2$—). Phases: X 48 (10) S$_A$ 18 I.

Use Examples

The compounds from Examples 1 to 4 are in each case added to 10% by weight of a smectic liquid-crystalline test mixture (TLC1) having an S$_A$—N phase-transition temperature of 91° C.:

| Substance from Example (10% by weight in TLC1) | S$_A$-N Phase-transition temperature |
|---|---|
| 1 | 86 |
| 2 | 75 |
| 3 | 89 |
| 4 | 89 |

It can be seen that in all cases the S$_A$—N phase transition is shifted to low temperatures, which is advantageous for certain applications, for example the utilization of the electroclinic effect.

We claim:

1. A liquid crystal mixture comprising one or more compounds of the formula I

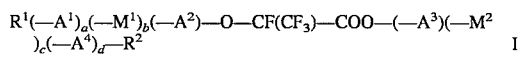

I in which the symbols and indices have the following meanings:

R$^1$ and R$^2$ are identical or different and are hydrogen, a straight-chain or branched alkyl radical having 1 to 20 carbon atoms (with or without asymmetrical carbon atoms), where one or more —CH$_2$— groups may also be replaced by —O—, —CO—, cyclopropane-1,2-diyl, —Si(CH$_3$)$_2$—, with the proviso that oxygen atoms must not be bonded directly to one another, and/or one or more H atoms of the alkyl radical may be substituted by —F;

M$^1$ and M$^2$ are identical or different and are —CO—O—, —O—CO—, or a single bond;

A$^1$, A$^2$, A$^3$ and A$^4$ are identical or different and are 1,4-phenylene, in which one or more H atoms may be replaced by F, pyrazine-2,5-diyl, in which one or two H atoms may be replaced by F, pyridazine-3,6-diyl, in which one or two H atoms may be replaced by F, pyridine-2,5-diyl, in which one or more H atoms may be replaced by F, pyrimidine-2,5-diyl, in which one or two H atoms may be replaced by F, trans-1,4-cyclohexylene, 1,3,4-thiadiazole-2,5-diyl, 1,3-dioxane-2,5-diyl, 1,3-dithiane-2,5-diyl, 1,3-thiazole-2,4-diyl, in which one H atom may be replaced by F, 1,3-thiazole-2,5-diyl, in which one H atom may be replaced by F, thiophene-2,4-diyl, in which one H atom may be replaced by F, thiophene-2,5-diyl, in which one or two H atoms may be replaced by F, naphthalene-2,6-diyl, in which one or more H atoms may be replaced by F;

a, b, c and d are zero or one with the exception of phenyl phenoxytetrafluoropropionate.

2. The liquid crystal mixture as claimed in claim 1, wherein the symbols and indices in the formula (I) have the following meanings:

$R^1$ and $R^2$ are identical or different and are hydrogen, or a straight-chain or branched alkyl radical having 1 to 18 carbon atoms (with or without asymmetrical carbon atoms), where one or more —CH$_2$-groups may also be replaced by —O—, with the proviso that oxygen atoms must not be bonded directly to one another, and/or one or more H atoms of the alkyl radical may be substituted by —F;

$M^1$ and $M^2$ are identical or different and are —CO—O—, —O—CO—, or a single bond;

$A^1$, $A^2$, $A^3$ and $A^4$ are identical or different and are 1,4-phenylene, in which one or more H atoms may be replaced by F, pyrazine-2,5-diyl, in which one or two H atoms may be replaced by F, pyridazine-3,6-diyl, in which one or two H atoms may be replaced by F, pyridine-2,5-diyl, in which one or more H atoms may be replaced by F, pyrimidine-2,5-diyl, in which one or two H atoms may be replaced by F, trans-1,4-cyclohexylene;

a, b, c and d are zero or one.

3. The liquid crystal mixture as claimed in claim 1, wherein the symbols and indices in the formula (I) have the following meanings:

$R^1$ and $R^2$ are identical or different and are a straight-chain or branched alkyl radical having 1 to 16 carbon atoms, where one —CH$_2$— group may also be replaced by —O—, and/or one or more H atoms of the alkyl radical may be substituted by —F, $M^1$ and $M^2$ are identical or different and are —CO—O—, —O—CO—, or a single bond;

$A^1$, $A^2$, $A^3$ and $A^4$ are identical or different and are 1,4-phenylene;

a, b, c and d are zero or one.

4. The liquid crystal mixture as claimed in claim 1, wherein the radicals $R^1(-A^1)_a(-M^1)_b(-A^2)$ and $R^2(-A^4)_d(-M^2)_c(-A^3)$ in the compounds of the formula (I) are identical.

5. A compound of the formula (I) as claimed in claim 1.

6. An electro-optical switching and display element comprising a liquid-crystal mixture as claimed in claim 1.

7. A liquid crystal mixture comprising 4-(5-octyloxypyrimidin-2-yl)phenyl 2,3,3,3-tetrafluoro-2-[4-(5-octyloxypyrimidin-2-yl)phenoxy]propionate.

* * * * *